US012178916B2

(12) United States Patent
Schaub (10) Patent No.: US 12,178,916 B2
(45) Date of Patent: Dec. 31, 2024

(54) COMPOSITIONS AND TREATMENT PROCEDURES FOR THE TREATMENT OF PATHOGENIC INFECTIONS

(71) Applicant: Walter Schaub, Hedingen (CH)

(72) Inventor: Walter Schaub, Hedingen (CH)

( * ) Notice: Subject to any disclaimer, the term of this patent is extended or adjusted under 35 U.S.C. 154(b) by 0 days.

(21) Appl. No.: 16/610,662

(22) PCT Filed: May 4, 2018

(86) PCT No.: PCT/EP2018/061607
§ 371 (c)(1),
(2) Date: Nov. 4, 2019

(87) PCT Pub. No.: WO2018/202897
PCT Pub. Date: Nov. 8, 2018

(65) Prior Publication Data
US 2021/0259974 A1    Aug. 26, 2021

(30) Foreign Application Priority Data
May 4, 2017   (CH) .................................. 00599/17

(51) Int. Cl.
*A61K 33/00*    (2006.01)
*A61K 8/20*    (2006.01)
(Continued)

(52) U.S. Cl.
CPC .......... *A61K 9/2009* (2013.01); *A61K 9/0053* (2013.01); *A61K 9/2013* (2013.01);
(Continued)

(58) Field of Classification Search
CPC ..... A61K 9/2009; A61K 9/0053; A61K 33/00
See application file for complete search history.

(56) References Cited

U.S. PATENT DOCUMENTS 4,689,169 A * 8/1987 Mason ................... A01N 59/00
                                                     252/186.24
5,312,626 A * 5/1994 Gergely ................. A61Q 11/00
                                                     424/44
(Continued)

FOREIGN PATENT DOCUMENTS

CN    101228868 B  *  6/2010
CN    101933938 A     1/2011
(Continued)

OTHER PUBLICATIONS

Kim et al. (Korean J PHysiol Pharmacol 2015;19:21-27) (Year: 2015).*

(Continued)

*Primary Examiner* — Ernst V Arnold
(74) *Attorney, Agent, or Firm* — Sughrue Mion, PLLC (57) ABSTRACT

Pharmaceutical compositions, and dosage forms thereof, comprising an oxidation agent selected from sodium, potassium, magnesium or calcium hypochlorite, chlorite or chlorate, an artemisinin composition or a derivative or combination thereof as a primary active oxidizing agent, which primary active oxidizing agent is provided in a form to enable release or generation of a hypochlorite ion or hypochlorous acid, a chlorite ion or chlorous acid, a chlorate ion or chloric acid, neutral or ionic chlorine dioxide or other derivative thereof from the respective hypochlorite, chlorite, or chlorate. The pharmaceutical compositions may be employed or administered to a warm-blooded mammalian subject to be treated for combatting pathogenic infections or invasions.

3 Claims, 2 Drawing Sheets (51) Int. Cl.
*A61K 9/00* (2006.01)
*A61K 9/20* (2006.01)
*A61K 31/366* (2006.01)

(52) U.S. Cl.
CPC ............ *A61K 9/2027* (2013.01); *A61K 9/205* (2013.01); *A61K 31/366* (2013.01); *A61K 33/00* (2013.01)

(56) References Cited

U.S. PATENT DOCUMENTS

| | | | | |
|---|---|---|---|---|
| 5,900,420 | A | * | 5/1999 | Cole ................ A61P 25/04 514/289 |
| 6,099,861 | A | * | 8/2000 | DeSenna ............ A01N 59/00 424/465 |
| 6,165,505 | A | * | 12/2000 | DeSenna ............ A01N 59/00 514/970 |
| 6,251,372 | B1 | | 6/2001 | Witt et al. |
| 6,280,761 | B1 | * | 8/2001 | Santus ............... A61P 25/32 424/440 |
| 6,846,478 | B1 | * | 1/2005 | Doyle ............... A61Q 11/00 424/49 |
| 2006/0258716 | A1 | | 11/2006 | Marash et al. |
| 2009/0078911 | A1 | | 3/2009 | Shibata et al. |
| 2010/0260812 | A1 | | 10/2010 | Hratko et al. |

FOREIGN PATENT DOCUMENTS

| | | | | |
|---|---|---|---|---|
| EP | 1797170 | A1 | * 6/2007 | ............ A23K 50/10 |
| GB | 608069 | A | 9/1948 | |
| JP | 11-511486 | A | 10/1999 | |
| JP | 2004-536137 | A | 12/2004 | |
| JP | 2007-217239 | A | 8/2007 | |
| JP | 4083983 | B2 | 4/2008 | |
| JP | 2011-037814 | A | 2/2011 | |
| JP | 2012-517956 | A | 8/2012 | |
| JP | 2015-104686 | A | 6/2015 | |
| WO | 89/03179 | A1 | 4/1989 | |
| WO | 97/33567 | A1 | 9/1997 | |
| WO | 99/39574 | A2 | 8/1999 | |
| WO | 99/43294 | A1 | 9/1999 | |
| WO | 03/009802 | A2 | 2/2003 | |
| WO | 2010/096300 | A2 | 8/2010 | |
| WO | WO-2016196440 | A1 | * 12/2016 | ........... A61K 31/327 |

OTHER PUBLICATIONS

Pharmaceutics The Science of Medicine Design (2013, OUP Oxford; p. 30; 2 pages). (Year: 2013).*
Google translation of CN101228868B; 2008; 25 pages. (Year: 2008).*
International Search Report for PCT/EP2018/061607 dated Aug. 23, 2018 (PCT/ISA/210).
Written Opinion for PCT/EP2018/061607 dated Aug. 23, 2018 (PCT/ISA/237).

* cited by examiner

COMPOSITIONS AND TREATMENT PROCEDURES FOR THE TREATMENT OF PATHOGENIC INFECTIONS

CROSS REFERENCE TO RELATED APPLICATIONS

This application is a National Stage of International Application No. PCT/EP2018/061607 filed May 4, 2018, claiming priority based on Swiss Patent Application No. 00599/17 filed May 4, 2017.

This invention relates to compositions and treatment procedures for the treatment of pathogenic infections.

BACKGROUND OF THE INVENTION AND STATE OF THE ART

An enormous amount of published information and literature is in existence concerned with the above subjects. The present invention is concerned with compositions and treatment procedures, which involve or include an oxidant as an active agent.

Accordingly, only exemplary information published prior to the effective date of the present invention, which are concerned with compositions which comprise an oxidant as an active agent, are summarised below.

The term "oxidant", as employed herein, is to be understood as a chemical compound or ion or atom (usually oxygen), which attracts and/or combines with electrons available from another composition of matter, more particularly, certain organic matter being or comprising one or more pathogens.

Broadly, pathogens, as employed herein, may be any one or more infectious disease entities such as a virus, bacterium, prion, fungus, viroid or parasite. Particular individual entities, such as a particular virus, bacterium or parasite may be individually identified and referred to as such herein.

Well known oxidants employed as disinfectants and in water, food and innate surface treatment procedures, include sodium or calcium chlorite ($NaClO_2$ or $Ca(ClO_2)_2$), sodium or calcium hypochlorite ($NaClO$ or $Ca(ClO)_2$), Chlorine dioxide (gaseous $ClO_2$ or ionic $ClO_2^-$ solutes), a chlorine component in the form of hypochlorous acid ($HOCl/OCL^-$), and ozone ($O_3$). Use of ozone as a disinfectant for topically treating wounds and for water treatment and sterilising surgical instruments is similarly well known. Ozone, however, has also been proposed for introduction into the human body and contentious therapies of presences in mammalian subjects of cancer, AIDS and other pathogenic diseases.

Compositions disclosed in the literature, which comprise an oxidant as an active agent in the sense employed herein, quite generally are limited to certain topical applications to mammalian species, including human and animal species. As indicated above, however, there have been earlier indications of introducing ozone into the human body, for example by means of an intravenous liquid ozone solution for treating various diseases. Overall, although so-called "ozone therapy" may be possessed of certain indicated merits, present views are that ozone therapy is unlikely to be practical. This for the reason that the US FDA, for example, has suggested that ozone therapy has no demonstrated safe medical application and, furthermore that in order for ozone to be an effective germicide, it would need to be present in a concentration greater than can be tolerated by man or other animals. This suggestion, at least in terms of the oxidative capacity of ozone represented by an affinity for electrons from organic structures, is considered to be supported by comparative studies related to chemical oxidation of dissolved organic matter by chlorine dioxide ($ClO_2$), chlorine as ($HOCl/OCl-$) and ozone ($O_3$) performed in Switzerland (Environ. Sci. Technol., 2013, 47 (19), pp 11147-11156). These comparative studies reflect that treatment with $ClO_2$ and HOCl resulted in prominent decreases in electron donating capacities, whereas treatment with $O_3$ resulted in only small decreases in electron donating capacities.

Chlorites, generally sodium chlorite, and hypochlorites, generally sodium or calcium hypochlorite, and chlorates are well known for use in the field of germicidal water treatment and general disinfection procedures. Also, mouthwashes, toothpastes and other oral care compositions comprising low concentrations of sodium chlorite are described in the literature or in Patents or Patent Applications. However, neither chlorites nor hypochlorites have been widely or seriously considered for use in pharmaceutical compositions rendered suitable for ingestion by or treatment of warm-blooded mammalian subjects.

Exemplary of the state of the art as is mentioned above is the conventional use in the food industry of sodium chlorite as an antimicrobial, and sterilisation of inanimate surfaces such as hospital rooms and surgical equipment. In international Publication Number WO 89/03179, published 20 Apr. 1989 (WO 89), reference is made to a dry pharmaceutical dosage form which might comprise 1) sodium chlorite powders or crystals; and 2) an inert material in admixture with the sodium chlorite. The admixture of sodium chlorite and inert material is indicated to generate chlorine dioxide ($ClO_2$) in an acidic aqueous solution. The acidic aqueous solution may be rendered acidic by the separate addition to a chlorite of an acidifying agent, or can be rendered acidic by the incorporation of a dry water-soluble acidifying agent into a chlorite dosage form composition. A typical pharmaceutical oral dosage form for use in destroying pathogens of the gastrointestinal tract is described, which includes:

7.199 mg of $NaClO_2$
75.2 mg of Milk Sugar (powder)
21.9 mg of Starch
20 mg of Talc
0.701 mg of Stearic Acid (powder).

Each such tablet would have a weight of 125 mg. Indicated is that typical acidifying agents which could be included which, when dissolved into an aqueous solution, would be sufficiently strong to react with the $NaClO_2$ to form $ClO_2$, e.g. powdered citric acid.

Importantly, the above WO 89 publication suggests that the mode of administration to a patient for purposes of destroying pathogens in the gastrointestinal tract, and indeed other described body cavities, invariably involve preliminary dissolution of the described tablets in water (which may be acidified or rely on acidification by stomach acid). For example, 500 ml. of water is required for the preparation of an aqueous solution for generating $ClO_2$ with the single 125 mg tablet as described above.

Publication WO 99/43294, published 2 Sep. 1999 (WO 99), is essentially concerned only with topical oral care compositions comprising a chlorite. Exemplary so-called "Dual Phase Dentrifice" compositions comprise amounts of sodium chlorite in combination with alkaline-acting compounds such as sodium bicarbonate, sodium carbonate and sodium hydroxide, no doubt for purposes of securing the indicated requirement for higher pH value media.

The claim forms of above WO 99 publication are directed solely to oral care compositions comprising up to about 12 mg of chlorite ion and less than at most 50 parts per million (ppm) chlorine dioxide or chlorous acid in the final aqueous medium. Forms of diseases of the oral cavity mentioned include plaque, gingivitis, periodontal disease, breath malador and whitening teeth, in humans or animals, by topically applying to the oral cavity, a safe and effective amount of chlorite ion.

The most common use of sodium chlorite is as a generator of chlorine dioxide for bleaching paper pulp and also for water treatment and disinfection procedures. Although also finding application in dilute forms in mouthwashes and as a preservative in cleaning solutions for contact lenses, sodium or potassium chlorite are not compounds which have been widely or seriously considered for use in pharmaceutical compositions suitable for any form of ingestion by or systemic exposure to warm-blooded mammalian subjects. This particularly so because, in solid form, sodium chlorite is unstable and solutions thereof are furthermore considered to be toxic and to cause symptoms similar to those suggested for sodium chlorate, i.e. ingestion of even small amounts may cause vomiting and nausea.

In view of the above-mentioned instability of sodium chlorite in solid form, this compound is indicated to be provided in stabilised admixed form together with sodium chloride, which may act both as a diluent and as a stabiliser. Tablets comprising sodium chlorite, excipients and other components, possibly including a quantity of a sodium chloride stabiliser and an organic acid, which generate chlorine dioxide when in aqueous solution, are commercially available in some countries. These tablets are indicated to be suitable for dissolution in smaller quantities of water and higher concentrations of chlorite, useful for topical application to carcass meat and other foods for disinfection purposes.

Also available is so-called "Stabilized Electrolytes of Oxygen (S.E.O)" which is an aqueous solution comprising a low concentration (3% w/v) of sodium chlorite. This solution has been suggested or indicated to provide red blood cell oxygenation properties when a sufficient quantity is ingested. Such use, however, has been deemed to be unacceptable or banned from use by many Health Authorities, including the US FDA.

Experimental reported uses involving oral administration of determined diluted dosage forms of aqueous solutions having a relatively high concentration (about 22.4% w/v) of sodium chlorite, colloquially known as "Miracle Mineral Solution" or "MMS". An acid (generally a 50% aqueous solution of citric acid) is separately added to the aqueous chlorite solution shortly before administration. This acidified solution is further diluted with water preliminary to oral ingestion to establish low concentration chlorite levels. Oral administration of such diluted solutions have been reported to provide effective results in treating a variety of patient conditions, such as patients harbouring malarial parasites, hepatitis, HIV and influenza viruses.

Some of above reports are based on use of an aqueous concentrate (28% w/v solution, actually 24% w/v) of sodium chlorite, involving addition of a prescribed amount of an acid, such as 1 spoonful of citric acid in 9 parts of water, by the patient or a medical assistant, to a prescribed amount (2 to 4×15 drops) of the chlorite concentrate solution, further diluted in water or a fruit juice. Indicated is that the acid component acidifies the basic chlorite and that an aqueous acidic environment leads to release of chlorine dioxide after about 3 minutes. Following on dilution of the acidified solution, it is advised that the concentration of $ClO_2$ falls to about 1 ppm. Suggested is that release of $ClO_2$ thereafter continues, but at a much slower rate.

In terms of the above reports, It is required that addition of the acid takes place very shortly (3 to 4 minutes) before administration. Dilution with half a glass of water or a fruit juice, once again by the patient or a medical assistant, precedes the following ingestion (by swallowing of the diluted solution) by the patient.

More recent reports are concerned with oral administration of a hypochlorite, more particularly calcium hypochlorite of water treatment or swimming pool quality. The particular product described is indicated to include an amount of non-toxic sodium chemicals such as sodium carbonate and sodium bicarbonate. Suggested is that the important characteristic is that the hypochlorite forms hypochlorous acid (HOCl) in aqueous solution, such as within the stomach of a subject. Indicated uses are for treating all kinds of cancer, at dosages ranging from 1 to 5 "0" size gelatine capsules filled with the calcium hypochlorite composition/day. Positive effects on cancer patients are reported. There are also cautionary reports concerned with whether or not the capsules should be taken before or after meals. A reported conclusion is that the capsules should pass through the stomach as quickly as possible before it dissolves, the reason being that hypochlorous acid immediately reacts with hydrochloric acid (in the stomach) to form toxic gaseous chlorine. Accordingly, the reported conclusion is to take a large amount of water on an empty stomach so that the capsule can pass into and dissolve in the duodenum (and thereby apparently alleviate or avoid formation of gaseous chlorine).

Literature discusses killing of asexual blood stages of *Plasmodium falciparum* parasites. Also, biochemical studies suggest that the anti-malarial effect of chlorine dioxide involves lysosomal trapping of the compound in the intra-erythrocitic parasite, followed by binding to the toxic hemin (the ferrous component of haemoglobin) produced during the course of haemoglobin consumption by the parasite. Such binding is indicated to prevent polymerisation of haemin to non-toxic malaria pigment. Chlorine dioxide is stated to penetrate the blood-brain barrier and accumulates in erythrocytes. The mechanism of action appears to be different from that of other antimalarial drugs, but may be related to the release of free radicals, similar to that which it is believed takes place when the peroxide bridge of Artemisinin is cleaved by iron ions. This cleavage is indicated to occur at high concentrations of hemin encountered by an Artemisinin active agent.

A complete review of Artemisinin, derivatives thereof and combinations with other active agents, artemisinin-based combinatory therapies (ACTs), which represent the best or most effective and widely employed products for the treatment of malarial parasites. However, more recent observations have advised of developments of resistance of *Plasmodium falciparum* to artemisinin products. These events, not reported here, have encouraged further developments in terms of the present invention.

Extended considerations which have been associated with the present invention have included references and potential appreciation of complex natural processes of enzymes, more particularly the peroxidase enzyme Myeloperoxidase (MPO) expressed in white cell neutrophil granulocytes. For example, it is understood to be generally well accepted that oxidation of MPO in the presence of chlorite ions, produces hypochlorous acid and heme as a cofactor. Similarly, the oxidation of tyrosine to form a tyrosyl radical appears to be similarly well accepted. Both the tyrosyl radical and hypochlorous acid are employed by the white cell neutrophil to inhibit growth or kill pathogens harboured by an infected subject.

The role of Phagocytes is available in the literature, but is not included here, although this may contribute to an understanding of the functioning of oxidants, the addition of which may contribute to or support immune reactions of warm-blooded mammalian subjects.

Of noted interest is the above literature is the express reference to a natural enzymatic process creating hypochlorite and that such hypochlorite is extremely toxic to bacteria.

SUMMARY OF THE INVENTION AND COMMENTS

In summary, the present invention relates to providing a number of compositions and treatment procedures for the treatment of pathogenic infections. The pathogenic infections may be such as comprised in conjunction with water or other liquids, foods, innate surfaces, invertebrates and warm-blooded mammalian subjects.

Components of the compositions essentially comprise an oxidant chemical compound which may be ionisable and generally include one or more oxygen atoms, which attract and/or combine with electrons available from another source of matter. Such source of matter is more particularly considered to include certain organic matter being or comprising one or more pathogens. The essential oxidant chemical compound comprised in the compositions of the invention may be generated by interaction between two or more components comprised in the composition. However, the oxidant chemical compound may be generated by the compositions following on exposure of the composition to an external interacting substance, such as may be presented by the environment or surface to which the composition is, is to be or may be applied.

Preferably, the compositions of the invention comprise aqueous medium or other solvent providing for dissolution of all or at least some components of the composition, for example thereby enabling ionic availability of ionisable oxidant chemical compounds comprised in the compositions. For example, an alkali metal salt of an oxidant such as a chlorite, hypochlorite, chlorate, carbonate, bicarbonate or oxide may provide for ionisation thereof in an aqueous solvent medium and thereby enable reaction with other components of the composition, such as an acidic component thereof.

The formulations or nature of the compositions to be employed for treating pathogenic infections may be made up of singular or multiple components may, following on dissolution in a solvent, more particularly an aqueous medium, be presented in solution of a tablet, particulate or granulate form. The compositions may thus be presented in solution or dispersion in a carrier medium, such as for use in applications to topical treatments of pathogenic infections or contaminated innate surfaces. Similarly, soluble or dispersed compositions may be presented for use as sprays for disinfection of enclosed spaces and also as sprays against invertebrates, such as mosquitos carrying or causing pathogenically active infections.

The concentrations of active oxidants and dosages of compositions of the invention as may be employed for uses and treatments of pathogenically infected warm-blooded mammalian subjects such as human subjects, is considered to depend largely on the nature of the pathogen infection, the severity of the infection, and the mode of administration.

Should the mode of administration be oral leading to enteral or gastro-internal tract (GIT) administration, it is noted that the dosage of certain oxidants in drinking water is limited to about 1 mg/l, equivalent to 1 part per million (ppm), such as in the case of sodium chlorite ($NaClO_2$). Presuming total absorption of the oxidant within the portal vein leading the oxidant to the liver, and presuming a lack of metabolism thereof by the liver, it appears that bioavailability of the oxidant in the systemic system of a healthy subject would be further diluted by the water content of an adult subject. It might be presumed that this water content might be about 50 litres. Thus, in terms of parts per million (ppm), the systemic bioavailability of oxidant level from oxidant-treated drinking water might be 1 ppm divided by 50=0.02 ppm. This value might represent the universally acceptable value of oxidant absorbed by a subject from oral ingestion of 1 l of drinking water.

In terms of the invention, it is believed and considered, based on confidential compassionate clinical trials in various African countries, that relatively high concentrations of oxidant may be successfully employed in treating patients suffering from pathogenic infections, more particularly malarial parasite infections, hepatic and other viral infections. Other treatments of pathogenic infections are considered to be likely to be successful, based on presently limited successful clinical trial experiences.

A procedure for employing a different mode of administration of oxidants considered to be of importance in terms of the present invention, is to assure avoidance of the exposure of oxidants to the contents of the GIT, more particularly, in the case of treating patients suffering from parasitical malarial infections and other pathogenic infections, including viral or other bacterial infections. The procedure, in terms of the invention, involves providing novel compositions comprising or releasing an oxidant which may be systemically absorbed without exposure to damaging effects of at least the digestive components of the GIT, as particularly represented by the contents of the stomach of subjects. This consideration is particularly applicable in relation to targeting pathogens located in the blood or plasma circulating system of patients, as in cases of malaria, dengue fever, Zika, Yellow fever and the like, potentially including certain forms of cancer, as reported in certain cases of the state of the art.

In the case of treating Hepatitis viral infections and perhaps also Hepatocellular carcinoma (HCC) located in the liver of subjects, targeting of the liver may preferably include or involve GIT absorption of active oxidants, so that the oxidant is absorbed in the portal vein leading to the liver of patients. However, clinical trials employing direct systemic absorption of oxidants have provided successful results, also with combatting Hepatitis B viral infections. Compositions for treating hepatitis infections, more particularly Hepatitis B, have comprised natural products, including Curcumin and/or Propolis known to be active for treating hepatitis. Successful treatments with such compositions have appeared after some days of treatment with higher dosages of oxidants, such as comprising repetitive administration of as much as 60 mg/l of direct systemically absorbable oxidant absorbable from the buccal cavity of treated subjects. Temporary side effects observed during treatments were limited to minor effects on gum recessions between the teeth of some subjects inclined to chew tablet forms of the compositions, in spite of the tablets being rapidly dissolved by saliva in the oral cavity within a few minutes. Alternative dosage forms, such as enterically coated tablet forms for enteral administration and granulate forms of the particular compositions are considered for such treatments.

In one aspect, the present invention is as set out in the claims. In a further aspect, the present invention relates to the following:

1. An essentially solvent-free solid composition for treating pathogenic or germicidal infections of materials such as liquids, foods, innate surfaces, invertebrates, volumes of air or infected mammalian subjects, comprising a primary oxidising agent selected from sodium, potassium, magnesium or calcium hypochlorite, chlorite or chlorate, an artemisinin composition or a derivative or combination thereof, in which at least said primary oxidising agent is water- or liquid-dispersible or water- or liquid-soluble to provide a liquid carrier medium for the primary oxidising agent which enables release or generation of a hypochlorite ion or hypochlorous acid, a chlorite ion or chlorous acid, a chlorate ion or chloric acid, molecular or ionic chlorine dioxide or derivatives thereof within the respective liquid carrier medium.

2. A composition according to 1, in which said primary oxidising agent is intimately admixed with with an acidic component to enable the liquid carrier medium within which the composition is or is to be dispersed or dissolved to be rendered acidic.

3. A composition according to 2, in which the acidic component is selected from anhydrous citric acid, gluconic acid, lactic acid, oxalic acid, tartaric acid, malic acid, ascorbic acid, stearic acid or a mixture of two or more of such acids.

4. A composition according to any one of 1 to 3, in which an amount of a carrier medium-dispersible or -soluble alkali or alkaline earth metal carbonate or bicarbonate salt is comprised in the composition.

5. A composition according to 4, in which the carbonate or bicarbonate salt is sodium or potassium carbonate or bicarbonate or a combination thereof.

6. A composition according to any one of 1 to 5, in which an amount of a carrier medium dispersible or soluble alkali or alkaline earth metal chloride is comprised in the composition.

7. A composition according to 6, in which the alkali metal chloride is sodium chloride or potassium chloride or a combination thereof.

8. A composition according to any one of 1 to 7, in which the composition is provided in a particulate, granulate or tablet form.

9. A composition according to any one of 1 to 8, in which the composition is an essentially solvent-free solid composition.

10. A composition according to any one of 1 to 9, in which the composition is protected from absorption or adsorption of water or particulate contaminants by means of a rupturable or openable air-impermeable, water-repellant enclosure enclosing the composition preliminary to rupturing or opening the enclosure for use in inhibiting or treating infections of water or an environment or surface for which the composition is or is to be employed.

11. A composition according to any one of 1 to 10, in which a pharmaceutically acceptable oral dosage form adapted for oral administration to a warm-blooded mammalian subject is provided for a prophylactic or treatment procedure of a subject likely to be exposed to or suffering from a pathogenic infection.

12. A pharmaceutical composition according to 11, in which said oral unit dosage form or a multiple thereof, comprises an absorbable therapeutically effective systemically non-toxic amount of said primary oxidation agent absorbable by transit through the gastrointestinal tract or other body cavity of a warm-blooded mammalian subject.

13. A pharmaceutical composition according to 11 or 12, in which said oral unit dosage form or a multiple thereof are adapted to be swallowed by the subject and thus become exposed to or further exposed to an acidic aqueous medium content of the stomach of the subject and thereby encourage release of highly water-soluble chlorine dioxide in absorbable form from the gastrointestinal tract, more particularly absorbed by absorption from the duodenum or small intestine of the subject.

14. A pharmaceutical composition according to 11 or 12, in which said oral unit dosage form or a multiple thereof are enteric-coated and rendered resistant to exposure to the acidic environment within the stomach of the subject to thereby allow for release of said primary active oxidising agent only in a section of the gastrointestinal tract downstream of or beyond the pylorus terminal end of the stomach of the subject.

15. A pharmaceutical composition dosage form according to 14, in which the enteric coating comprises a selection from cellulose acetate phthalate, cellulose acetate trimellitate, celluloseacetate succinate, hydroxypropylmethylcellulose acetate succinate, methacrylic acid/ethyl acrylate, hypomellose acetate succinate, hydroxypropyl methylcellulose phthalate, and Polyvinyl acetate phthalate, or a combination thereof.

16. A pharmaceutical composition according to any one of 10 to 14, in which said primary active oxidising agent is intimately admixed with an anhydrous acid in terms of 2 or 3 to enable a relatively pH-neutral or alkaline aqueous solvent medium within the gastrointestinal tract downstream of or beyond the pylorus end of the stomach of the subject to be rendered acidic and thereby encourage release of enterally-soluble chlorine dioxide for absorption into the blood-stream of the portal vein leading to the liver of the subject by absorption by the sites of absorption offered by the duodenum or small intestine of the subject.

17. A pharmaceutical composition according to 10, in which said primary active oxidising agent is intimately admixed with an anhydrous acid in terms of 2 or 3, and in which said oral unit dosage form or a multiple thereof are provided in a soluble lozenge form adapted to be retained in the mouth or buccal cavity by the subject and thus allow for release of said primary active oxidising agent within an acidic aqueous medium provided by simultaneous release of said water-soluble anhydrous acid into salivary contents of the buccal cavity and thereby enable direct systemic absorption of the primary active oxidising agent or derivative thereof through the absorptive surface area offered by the lining of the buccal cavity of the subject.

18. A pharmaceutical composition according to any one of 12 to 17, in which the composition comprises an amount of the primary active oxidising agent not exceeding about 5% w/w of the total weight of the composition.

19. A pharmaceutical composition dosage form according to any one of 15 to 18, in which the composition comprises a proportion of sodium bicarbonate or potassium bicarbonate or a combination thereof which is in excess of about 30% w/w of the total weight of the composition.

20. A pharmaceutical composition dosage form according to 11 to 19, in which the composition comprises a proportion of an alkali or alkaline earth metal chloride which is less than about 5% w/w of the total weight of the composition.

21. A pharmaceutical composition dosage form according to 20, in which the alkali metal chloride is sodium or potassium chloride.

22. A pharmaceutical composition dosage form according to any one of 11 to 21, in which the composition comprises pharmaceutically acceptable excipients, diluents, binders or other conventional excipients.

23. A pharmaceutical composition dosage form according to 22, comprising between zero to 88 mg of gum Arabic binder, a polyvinylpyrrolidone excipient, a sweetener such as Acesulfam K, a xylitol excipient carrier medium and a magnesium stearate talcum combination.

24. A pharmaceutical composition dosage form according to 23, in which exemplary unit dosage forms for oral administration to a warm-blooded mammalian subject is for a treatment procedure of a subject exposed to or suffering from a pathogenic infection or invasion, comprises the following exemplary admixed constituents, provided in the indicated approximate quantities:

| | | |
|---|---|---|
| Sodium bicarbonate | 44 mg | 44 mg |
| Sodium chlorite | 15 mg | 15 mg |
| Gum Arabicum | 44 mg | |
| Sodium chloride | | 14 mg |
| Polyvinylpyrrolidone (Povidone 25) | 7 mg | 7 mg |
| Citric acid | 65 mg | 65 mg |
| Acesulfam K | 2 mg | 2 mg |
| Xylitab | 376 mg | 406 mg |
| Prosolve | 30 mg | 30 mg |
| Talcum/Magnesium stearate (40%) | 50 mg | 50 mg |
| Total | 633 mg | 633 mg |

25. A pharmaceutical composition dosage form according to 2, in which exemplary unit dosage forms for oral administration to a warm-blooded mammalian subject is for a treatment procedure of a subject exposed to or suffering from a hepatitis pathogenic infection or invasion, comprises the following exemplary admixed constituents, which include soluble curcumin and/or propolis provided in the indicated approximate quantities:

| | | |
|---|---|---|
| Sodium bicarbonate | 44 mg | 44 mg |
| Sodium chlorite | 15 mg | 15 mg |
| Curcumin and/or Propolis (soluble) | 11-22 mg | 11-22 mg |
| Sodium chloride | | 14 mg |
| Polyvinylpyrrolidone (Povidone 25) | 7 mg | 7 mg |
| Citric acid | 65 mg | 65 mg |
| Acesulfam K | 2 mg | 2 mg |
| Xylitab | 376 mg | 406 mg |
| Prosolve | 30 mg | 30 mg |
| Talcum/Magnesium stearate (40%) | 50 mg | 50 mg |
| Total | 600-611 mg | 704-715 mg |

25. A pharmaceutical composition dosage form according to any one of 16 to 22, in which the proportion of the primary active oxidising agent in the composition is selected to provide a concentration of active agent within the aqueous medium available in a selected body cavity of the mammalian subject is less than about 100 ppm.

26. A pharmaceutical composition dosage form according to any one of 9 to 23, in which the pharmaceutically acceptable active concentration level of said primary active oxidising agent in said aqueous medium is selected to control the level or rate of systemic absorption from said aqueous medium into the plasma or blood stream of the subject by absorption sites of the gastrointestinal tract or other body cavity to obtain a pharmaceutically acceptable active concentration level of the primary active agent in said plasma or blood stream.

DETAILED DESCRIPTION OF COMPOSITIONS AND TREATMENTS

Overall, the germicidal compositions described in certain state of the art mentioned above concern application of aqueous solutions, either topically or within a body cavity, considered to be equivalent to topical application, or to inanimate surfaces, such as surgical instruments or the like. Systemic applications involving absorption and distribution or release of a chlorite, hypochlorite, or chlorine dioxide generated within the gastrointestinal tract of a warm-blooded mammalian subject, such as for purposes of deactivating systemic viral or other systemic pathogenic infections, are similarly considered.

At the same time as the above suggestions of positive indications of successful clinical uses of both chlorites and hypochlorites, there exists a broad spectrum of skepticism in the medical profession (and banning by Health Authorities) related to any form of administration of chlorite or hypochlorite to a patient, irrespective of the condition to be treated. In this regard, it is considered or believed that much of the skepticism arises from reported cases of nauseous reactions, vomiting and other reactions which take place following on ingestion of such active agents. For example, in the case of administration of a hypochlorite such as calcium hypochlorite, the hypochlorite may generate chlorine gas in the hydrochloric acid environment of the stomach, as discussed above. The reasons for similar reactions in the case of administration of chlorites is not clear, but is likely to be related to reactions with hydrochloric acid and other acidic components including digestive enzymes and flora within the stomach of the patient. In any event, it is apparent that much of the suggested desired formation of chlorine dioxide available for absorption would not be controllable and would vary widely from patient to patient and furthermore be dependent on patient conditions and the intended treatment.

This invention relates to compositions comprising an oxyanion chlorite, hypochlorite, chlorate or other oxidant. The invention is concerned with novel compositions and specified oral dosage forms of pharmaceutical chlorite, hypochlorite or chlorate oxidants and possibly further oxidants, which may be employed under certain specified conditions and dosage forms for administration to warm-blooded mammalian subjects suffering from the presence of a pathogenic infection.

Based on reported and observed positive clinical results obtained with treatments involving ingestion of low concentration aqueous solutions of sodium chlorite and release of active chlorine dioxide and also an encapsulated form of solid calcium hypochlorite forming hypochlorous acid, further studies have been conducted to determine if means can be developed for gaining control over undesirable side effects on patients following on administration of aqueous chlorite solutions, capsules of hypochlorite or other oral dosage forms. These further studies have also been performed in view of the development of tolerance or resistance of parasites, such as malarial parasites, to presently available medication, including Artemisinin preparations. Also accounted for is the fact that infectious diseases are prevalent in poverty-stricken urban and remote areas, which means that the product should most preferably be stable, readily accessible and inexpensive.

Accordingly, one objective of this invention is to provide pre-prepared, stable and specially adapted pharmaceutical oral dosage forms comprising a chlorite, hypochlorite or chlorate or possibly also or alternatively dissolved chlorine dioxide, hypochlorous acid or chloric acid oxidant, together with optional or necessary further conventional components of pharmaceutically acceptable components, such as stabilising agents, pH adjustment components, generally an acid such as citric acid to lower the pH of high pH oxidants, a lower pH (lower than that of the oxidant) diluent compound such as sodium bicarbonate, a reducing agent such as sodium or potassium chloride, binding agents, excipients, sweeteners and further inert excipients.

In accordance with confidential studies related to the invention, an exemplary solid unit oral dosage form of a pharmaceutical composition has been developed and employed in clinical trials on a confidential compassionate basis in several countries where malaria and other pathogenic infections are prevalent. This exemplary solid unit oral dosage form, within the scope of the present invention, comprises from about 5 mg to about 30 mg of sodium chlorite, intimately admixed with an amount of a solid dry anhydrous carboxylic acid sufficient to adjust the pH to physiological levels when in aqueous medium solution, and similarly enable at least a proportion of the oxychloro oxidant to form or release a corresponding equivalent amount of chlorine dioxide, ionic chlorine dioxide ($ClO_2$—) or chlorous acid ($HClO_2$) when the unit oral dosage form is exposed to or comprised within an established acidic aqueous medium environment.

Sodium chlorite is known to be a powerful oxidant available in trihydrate or anhydrite forms. The anhydrite in the above exemplary unit dosage form is a preferred form for use in pharmaceutical compositions of the invention, more particularly because of the dry conditions required for preparation and stability of the compositions. The anhydrite is hygroscopic, but does not agglomerate and is thus particularly suitable for admixing with other components of dry pharmaceutical oral dosage form compositions.

The solid carboxylic acid comprised in a dry unit oral dosage form of the invention may be any one of citric acid, glycolic acid, gluconic acid, lactic acid, oxalic acid, tartaric acid, malic acid, ascorbic acid, stearic acid or a mixture of two or more of such acids. Preferred, in view of ready availability and cost factors, is citric acid and the amount thereof comprised in a unit dosage form may be between about 20 mg to about 130 mg (optionally in conjunction with an amount of sodium chloride (−1 oxidation state) from about 5 mg to about 30 mg), which contributes to the stability of the composition.

Exemplary of the generation of chlorine dioxide is the following chemical reaction between the carboxylic citric acid and sodium chlorite in an aqueous medium:

A similar reaction occurs with sodium or potassium hypochlorite to generate a hypochlorite (ClO—) ion A unit dosage form of the invention may comprise components of an effervescent agent; one component thereof may be an amount of the carboxylic acid comprised in the composition (in excess of that amount required for generating chlorous acid and ionic or molecular chlorine dioxide) and a further component thereof may be sodium or potassium bicarbonate providing for both dilution of the chlorite concentration in a solid oral unit dosage form, and furthermore enabling generation of carbon dioxide, or effervescence reactions following on reaction of a bicarbonate with an acid, should this be desirable.

The amount of sodium bicarbonate comprised in a unit dosage form may be from about 15 mg to about 90 mg depending on the amount of the chlorite and carboxylic acid amounts comprised in the unit dosage form. Thus, since the alkaline-acting sodium bicarbonate may consume a proportion of the carboxylic acid to produce an effervescent effect created by generation of gaseous carbon dioxide, the amount of the carboxylic acid, which may be the carboxylic citric acid, should exceed the equivalent amount of the sodium bicarbonate by at least that amount required to generate a desired amount or concentration of chlorous acid or ionic chlorine dioxide from the chlorite. However, it is preferred that the amount of bicarbonate comprised in a unit dosage form be intimately admixed with a dedicated acidifying agent to enable carbon dioxide to be generated. A preferred acidifying agent for this particular purpose is disodium pyrophosphate, conventionally employed in certain baking powder bicarbonate compositions.

The stability of solid sodium chlorite is enhanced by the presence of a chloride in the compositions of the invention and, once again, is dependent on the amount of sodium chlorite present. Since a chloride is not an essential component of the compositions of the invention, the amount of the chloride in the above unit dosage form may, for example, be from zero to about 28 mg (of sodium chloride).

A gum Arabic binder may be included in compositions of the invention in suitable amounts, such as between zero to 88 mg in a unit dosage form. Similarly excipients such as a polyvinylpyrrolidone, a sweetener such as Acesulfam K, a xylitol excipient carrier medium and talcum/magnesium stearate, may be comprised in required or preferred amounts in unit dosage forms.

An important characteristic of preferred oral dosage forms of the invention is related to the objective to avoid, as well as is possible, that the oxidant not be exposed to the acidic environment of the gastric juices within the stomach of a subject, which may cause toxic effects. The preferred mode of administration has accordingly thus far been indicated to retain a unit dosage form sublingually in the mouth and to allow active components thereof to dissolve and react in the aqueous medium of the saliva of the patient.

The pH of saliva in the oral cavity of a human subject is normally about neutral to slightly alkaline, similar to that of the small intestine. Also, the mucous membrane defining the oral and nasal cavities of the subject provides absorption sites enabling direct absorption of desired active oxidant agents into the systemic blood stream of the patient without exposure to the low pH hydrochloric acid environment in the stomach of the subject. Furthermore, since the contents of the stomach also comprise the acidic digestive pepsin enzyme, quantities of chlorite, chlorous acid or chlorine dioxide made available in the stomach of the subject by enteral administration of a composition of the invention, are likely to be lost and therefore avoided from enabling absorption.

Subjects treated with the oxidant compositions of the invention as above, have during clinical trials have been encouraged to avoid or limit swallowing of the solid oral dosage form itself, precisely to avoid reactions of active agent in the stomach of patients. During dissolution sublingually in the aqueous saliva in the mouth, the acid, oxidant and water interact to form ionic chlorite, hypochlorous acid and a highly water-soluble neutral or ionic chlorine dioxide solute. These components or solutes, generated within the oral cavity have been determined to be readily absorbed into the plasma of the systemic blood stream of subjects directly across the mucous membrane lining of the oral and perhaps nasal cavities.

As previously partially discussed, insofar as the generation of readily soluble gaseous chlorine dioxide by the unit dosage form may take place, the dosage forms of the invention furthermore and most preferably comprise an amount of a bicarbonate such as potassium or sodium bicarbonate. The bicarbonate in dry form serves to provide for solid dilution of the alkaline oxidation chlorite hypochlorite or chlorate solid components and may simultaneously serve to generate gaseous carbon dioxide or form carbonic acid in aqueous medium. The bicarbonate content, generally together with inert carriers and binders, advantageously lower the concentration of the oxidant solutes and consequential formation in aqueous medium of chlorine dioxide or chlorous acid. In the case of a hypochlorite solute, carbon dioxide ($CO_2$) advantageously contributes by means of availability thereof to formation hypochlorous acid (see "Some possible reactions involving a hypochlorite" below).

The quantitative selection of amounts of bicarbonate, active chlorite or hypochlorite and inert components, more particularly a volume expanding water-soluble binder, provides for the integrity and distribution of intimately admixed components of dry oral dosage forms of the invention. Similarly, the rate of dissolution of components from the dosage form into a selected aqueous medium of a subject may effectively be controlled by means of inert carrier or binder substances, which is considered to be an important consideration involved in the present invention. This more particularly so because the concentration of components in surrounding aqueous medium of a subject may in this fashion be limited to pharmaceutically acceptable levels and consequently the rate of absorption into the blood stream of the subject across mucous membrane lining comprising the aqueous medium may similarly be controlled and once again limited to pharmaceutically acceptable active levels.

In the case of the oxidant component being a calcium or magnesium compound, even at the preferably low concentration levels thereof, the presence of a carbonate or bicarbonate may lead to precipitation complications. However, in view of the majority of patients requiring treatment being in a condition of metabolic acidosis and lacking an adequate or normal level of bicarbonate buffer (less than 20 mEq/l, usually as measured in arterial blood) absorption of bicarbonate could provide additional beneficial support to subjects requiring treatment.

The mildly alkaline bicarbonate content furthermore provides for improved mouth feel and taste. Such lowering of concentrations of chlorites or hypochlorites also lowers the potential of local irritation of the oral and nasal mucous membranes linings as may be caused by exposure to strong oxidising agents and possible generation of excessive concentrations of chlorine dioxide and possible minor quantities of chlorate and chlorine gas. An adequate concentration of sodium chloride, however, similarly contributes to lowering risks of damage to mucous or other linings of the gastrointestinal tract.

Specific examples of two similar unit lozenge type dosage forms of the above chlorite compositions for use in the oral cavity of a subject, each comprising identical amounts of chlorite and acid, and each comprising a preferred high sodium bicarbonate content, are set forth below:

| EXAMPLES: | I | II |
|---|---|---|
| Sodium bicarbonate | 44 mg | 44 mg |
| Sodium chlorite | 15 mg | 15 mg |
| Gum Arabicum | 44 mg | |
| Sodium chloride | | 14 mg |
| Polyvinylpyrrolidone (Povidone 25) | 7 mg | 7 mg |
| Citric acid | 65 mg | 65 mg |
| Acesulfam K | 2 mg | 2 mg |
| Xylitab | 376 mg | 406 mg |
| Prosolve | 30 mg | 30 mg |
| Talcum/Magnesium stearate (40%) | 50 mg | 50 mg |
| Total | 633 mg | 677 mg |

| EXAMPLES for HEPATITIS: | I | II |
|---|---|---|
| Sodium bicarbonate | 44 mg | 44 mg |
| Sodium chlorite | 15 mg | 15 mg |
| Curcumin and/or Propolis (soluble) | 11-22 mg | 11-22 mg |
| Sodium chloride | | 14 mg |
| Polyvinylpyrrolidone (Povidone 25) | 7 mg | 7 mg |
| Citric acid | 65 mg | 65 mg |
| Acesulfam K | 2 mg | 2 mg |
| Xylitab | 376 mg | 406 mg |
| Prosolve | 30 mg | 30 mg |
| Talcum/Magnesium stearate (40%) | 50 mg | 50 mg |
| Total | 600-611 mg | 704-715 mg |

In the above example, an amount of Artemisin amounting to about 2 mg may be included. Furthermore, for purposes of treating cancer patients, the Curcumin and/or Propolis component comprised in the above example may be replaced by by an extract from Graviola, a South American plant known or newly suggested to be of increased efficacy in the treatment of cancers. The suggested amount of the Graviola extract in the above example has been indicated to be as much as 30 mg Clinical trial treatments employing buccal administration of compositions in terms of the above examples for treating subjects suffering from hepatitis viral infections, have provided successful results in all of an exemplary present total of 8 female and male cases of hepatitis B virus (HBV) infections with low copies or low International Units (IU). In all cases, conventional detections performed before and after treatments, provided quantitative viral load (copies/ml, log 10, and IU/ml) measures after treatment which were below the limit of detection of 200 copies/ml or 50 IU/ml.

Dosages of the lozenge tablets are dependent on the body-weight of the patient, patient condition, and the nature and severity of the pathogen harboured by the patient. In the example of the pathogen being a malaria parasite, relatively high dosages have been employed to ensure an adequate temporary release of chorine dioxide in the saliva of the patient and adequate absorption enabling growth of the malaria parasite to be inhibited and finally destroyed altogether from the blood stream of the patient. Thus, for example, in the case of adults and children over 12 years old, as many as 5 to 6 lozenge tablets of the nature of the above examples are initially prescribed to be administered to the oral cavity every two hours. During an initial period of the two-hour period, the lozenge tablets relatively slowly dissolve and disintegrate in the saliva of the patient. The active agents release active chlorine dioxide or chlorous acid solutes in the saliva, which solutes are simultaneously slowly absorbed into the systemic plasma or blood stream directly through the mucous membrane of the oral and possibly nasal cavities of the subject. Generally, gaseous chlorine dioxide diluted by carrier gaseous carbon dioxide is formed in the saliva and systemically absorbed by the subject from this solute condition.

The above dosage regimen, is prescribed based on a regular necessity to rapidly inhibit parasitical pathogen or viral growth and also, as rapidly as is possible, reach and deactivate all parasitical pathogen or viral invasions. Employment of a relatively aggressive dosage regimen, dependent on compliance factors, should generally lead to treated subjects being free of parasitical or viral infections within a few days, regularly within two days in the case of malaria parasite infections. In some cases, where adequate effects are not experienced, the recommended successive two-hour dosages may be increased to as many as 7 lozenge tablets.

Toxicity and side-effect issues, such as nausea, vomiting and the like, known for chlorite composition ingestion are, perhaps surprisingly, not encountered by patients having received treatment with the lozenge dosage form products of the present invention. The lack of toxicological effects is at least partially attributed to maintaining slow absorption of active agent, followed by relatively low absorption concentrations thereof offered by absorption sites of the linings within the buccal cavity. A further factor considered to be of importance is that the absorbed active chlorine dioxide provides selective activity and attacks and, for example in cases of viral diseases, disrupts only the cellular membrane of parasitical and viral cellular infections. Of further importance is the fact that the potentials of toxicological effects of oxygenator compounds, such as represented by requirements for very low contents of oxidants in drinking water, are eliminated precisely by the reaction of the oxidants with pathogenic infections comprised within the systemic system of the subject, including such infections located in the liver of the subject. Thus, as also confirmed by the confidential studies related to the invention reported below, the confidential studies related to the invention provide indications that the oxychloro oxidant convert to water and sodium chloride following on reaction with cellular located pathogens which comprise electron-donating centres. ^

Considerations such as above, more particularly the locality of release in the essentially neutral aqueous environment of the buccal cavity has prompted initiating further developments of dosage forms which enable acceptably low rate release in lower regions of the gastrointestinal tract, such as in the moderately acidic aqueous medium of the duodenum or probably preferably the moderately alkaline small intestine where the principal absorptive surface area is available. Accordingly, the present invention also contemplates such compositions.

Although it is preferred that lozenge compositions such as above have thus far generally been employed in clinical trials in the fashion described above, i.e. retained in the mouth and allowed to dissolve and react in the saliva of the subject, some of the clinical trials performed and reported below are likely to have included inadvertent or uncontrolled swallowing of one or more unit dosage forms or solutions thereof. However, no harmful or toxic effects were observed in any of the patients treated.

An example of a series of demonstrations of clinical efficacy is reported below in relation to compassionate treatment of 50 patients of various ages. All patients had shown acute symptoms of malarial infection. The patients were determined to be *Plasmodium falciparum* positive as indicated by their blood count at their first visit to the local medical practitioner. Patients, including a number of small children, were advised to consume (by release within the mouth) a relatively low daily dosages (as compared to accelerated dosages over a short 2-day period at 5 to 7 lozenge tablets every two hours as mentioned above) involved administration of an earlier prototype product named VCR Tablets. Three tablets during a day were prescribed, resulting in a total dosage of 45 mg of sodium chlorite per day. Following on a second and third visit to the medical practioner, the blood of each patient was screened for *Plasmodium falciparum* at day four and day six, and symptoms and side effects of the medication recorded. The ages and genders of the patients and reported side effects are shown in the Table below:

| AGE (range years) | 1-4 | 5-20 | 21-50 | >50 |
|---|---|---|---|---|
| GENDER (male/female) | 2/0 | 8/10 | 10/14 | 2/4 |
| No. of patients | 2 | 18 | 24 | 6 |
| Side effects of therapy | none | none | none | |

Figure 1:
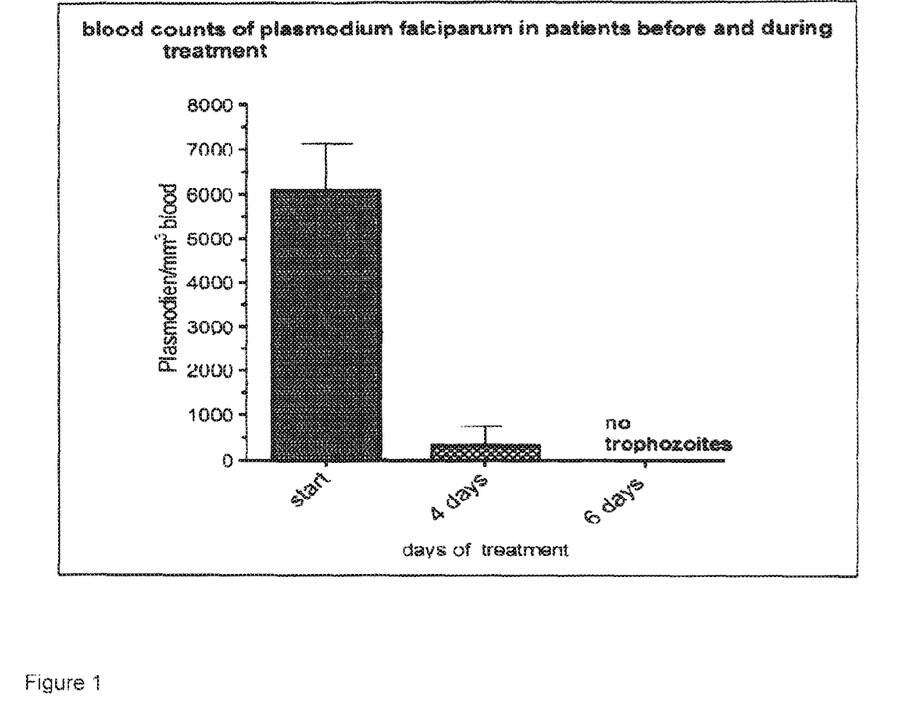
FIG. 1 shows the mean count for positive *Plasmodium falciparum* at the start of the study and at 4 and 6 days after treatment. The mean count of *Plasmodium falciparum* per $mm^3$ of blood is shown.

As can be seen from FIG. 1, the mean count for positive *Plasmodium falciparum* before the start of the study was 6084 (±1038 SD/Standard Deviation) trophozoites/mm$^3$. Following on the therapy, the number of *Plasmodium falciparum* had dropped to a mean count of 321 trophozoites/mm$^3$ (±63 SD) at day four, and no or zero trophozoites were detected in the blood at day 6.

In parallel with the above spectacular decline in microbes, an overall rapid recovery in the well-being of the patients could be observed and none of the preexisting symptoms were observed or reported by the patients. Furthermore, none of the patients dropped out of the study because of intolerance.

In parallel with the above spectacular decline in microbes, an overall rapid recovery and overall feeling of wellbeing of the patients could be observed and none of the preexisting symptoms were observed or reported by the patients. Furthermore, none of the patients dropped out of the study because of intolerance, such as for reasons of vomiting or nausea reported for ingestion of other earlier chlorite, hypochlorite or chlorine dioxide compositions.

Considered to be of importance in relation to the above treatment procedure involved with the present invention, is that the pharmaceutical preparation of the invention, which comprises a relatively high concentration of about 2% or 0.02 w/w sodium chlorite, equivalent to 15 mg/l in 1 l saliva which would equate with 15 ppm, avoids exposure of the preparation to the contents of the stomach of the gastrointestinal tract and its variable hydrochloric acid and digestive acidic enzyme contents. As compared to other preparations suggested to be suitable for ingestion with quantities of water for the treatment of gastrointestinal infections, concentrations of chlorite for reaction with an acidic medium for purposes of generating hypochlorous acid or chlorine dioxide would not exceed at most 15 ppm of an administered solution for fear of damaging locally exposed tissue cells.

Following on further developments of chlorite or hypochlorite-containing oral dosage forms of the invention, consideration has more recently been given to substantially increasing the bicarbonate content to as much as 900 mg in a solid 1000 mg unit oral dosage form. However, having regard to the size of such an oral dosage form, the total amount of all constituents would conveniently or preferably not exceed about 600 mg.

Although the significance or relevance of immune responses, as related to the present invention have thus far not been considered in detail, independent literature suggests that immune responses on their own, appear not to be adequate to protect a host against certain invading pathogens and that administration of products of the present invention may provide possible support or accelerate innate immune responses. Thus, bearing in mind that, where innate immunity response does fail, as is for example the case where an invading pathogen has developed resistance to conventional treatments, the possibility might exist in certain cases of pathogen invasions, for these antigens to be detected and attacked by mechanisms of adaptive immunity responses. However, unlike the constitutively present innate immune system, which should generally react promptly to infections, adaptive immune response requires time (in general some days) to develop. Indeed it appears that adaptive immunity may in certain cases of pathogen invasion simply be too late to effectively combat infections which have, during this development time, spread widely in the infected host and caused irreparable damage to the host, such as to tissue cells and organs.

Innate and adaptive immune responses each function to protect the host against invading organisms, although their protective functions differ. However, considered to be of importance in terms of the present invention, is that innate immunity response mechanisms which are present in a subject at all times and generally provide immediate protection against most invading pathogens, an additional and important function of innate immune response is to activate adaptive immune response mechanisms.

Oxidation of Myeloperoxidase (MPO) in the presence of chlorite ions, produces hypochlorous acid and heme as a cofactor. Similarly, the oxidation of tyrosine to form a tyrosyl radical, which together with hypochlorous acid are employed by the white cell neutrophils to inhibit growth or kill pathogens harboured by an infected subject. Having regard to the delay for adaptive immunity reactions to take place, more particularly believed to be for reasons of delayed activation of such adaptive immunity reactions by innate immunity reactions, a procedure for providing a systemically absorbable or resorbable chlorite or hypochlorous acid directly to an infected subject might be indicated. Thus, the chlorite or hypochlorite which produces hypochlorous acid or the more active chlorine dioxide in acidic medium, is accordingly rendered to be promptly or immediately available for direct contact and reaction with the ubiquitous and abundant ferrous haeme cofactor, as is indicated to be produced by the oxidation of Myeloperoxidase (MPO) in the presence of chlorite ions. The reactivity of the innate immunity reactions, more particularly the activation of adaptive immune response, it is suggested might be accelerated and accordingly reduce the time for adaptive immunity reactions to take effect.

At this point, in order to avoid regular confusion in chemical terminology, the presence of chemicals in the pharmaceutical compositions of the invention or those which may be generated in combination with others are set forth below, along with certain of the reactions which may take place upon exposure to an aqueous medium within sections of the gastrointestinal tract, including the buccal cavity:

Sodium or potassium chloride; NaCl or KCl
Sodium or potassium chlorite; $NaCO_2$ or $KClO_2$
Chlorous acid; $HClO_2$
Hypochlorous acid or hypochlorite ion; HOCl or $ClO^-$
Chlorine dioxide or ionic chlorine dioxide; $ClO_2$ or $ClO_2^-$
Calcium or sodium hypochlorite; $Ca(ClO)_2$ or NaClO
Some possible reactions involving a hypochlorite:

$$Ca(ClO)_2 + CO_2 \rightarrow CaCO_3 + Cl_2O \quad \text{(gaseous dichlorine monoxide)}$$

$$Cl_2O + H_2O \rightarrow 2HOCl \text{ or } 2H^+ + 2OCl^-$$

$$ClO^- + H_2O \rightarrow HOCl + OH^-$$

$$Ca(ClO)_2 + 4HCl \rightarrow CaCl_2 + 2H_2O + Cl_2 \quad \text{(gaseous chlorine)}$$

The main commercial use for sodium chlorate is for the preparation of chlorine dioxide ($ClO_2$). The largest application of $ClO_2$, which accounts for about 95% of the use of chlorate, is in bleaching of pulp. Reactions leading to generation of hypochlorous acid or hypochlorite ions, as in the second and third reactions above are considered to be favourable, whereas a reaction leading to generation of dichlorine monoxide (gaseous) and chlorine (gaseous), as in the first and fourth reactions are considered to be unfavourable. However, it is noted that dichlorine oxide may be obtained by reaction of calcium hypochlorite with carbon dioxide and that hypochlorous acid (a desirable product in relation to the present invention) is obtained following on reaction of dichlorine monoxide with water.

An experienced Research Chemist, Biochemist and Toxicologist who combined this experience with that of a Practicing Nutritionist and Natural Therapist, has commented on the use of calcium hypochlorite capsules for the treatment of prostate cancer and the HIV virus in the following terms: "When calcium hypochlorite dissolves in water, it forms hypochlorous acid. This is a stronger oxidant and more bactericidal than chlorine, and is also produced and used by the immune system. Hypochlorous acid reacts immediately with hydrochloric acid to form chlorine." The comments continue: "Therefore the idea is to get the capsule through the stomach as quickly as possible before it dissolves. When taking a large amount of water on an empty stomach then it goes through (the stomach) without much delay and the capsule can dissolve in the duodenum."

Although the absorption is mainly a function of the small intestine, some absorption of certain small molecules nevertheless does occur in the stomach through its lining. This includes:
Water, if the body is dehydrated
Medication, like aspirin
Amino acids
10-20% of ingested ethanol (e.g. from alcoholic beverages)
Caffeine Having regard to the possible reactions of a hypochlorite mentioned above, in combination with comments provided above, which are considered to be justified, a factor in terms of the present invention is to develop enteric coated pharmaceutical compositions of the invention, enabling release of the components thereof in the duodenum or rather in the slightly alkaline small intestine of a subject and thereby avoid release in the stomach of the subject. However, since absorption of certain desired generated components may take place from the stomach of the subject, the enteric coating may in some formulations, as for example described above, not be essential.

Enteric coating of an alkaline-acting composition, notably resistant to decomposition in acidic medium such as in the stomach of a subject, but decomposable in the neutral to slightly alkaline medium in the small intestine of a subject is in fact not a straight-forward task. Thus, for example, by virtue of the enteric coating being decomposable in a neutral to alkaline environment, alkaline-acting components such as present in compositions of the invention may decompose the enteric coating from within an enteric coated capsule or tablet or enteric-coated granulate particles.

The above potential difficulty, it is considered likely to be experienced with oral dosage form compositions of the present invention comprising a chlorite, hypochlorite or chlorate in view of the high alkalinity thereof. However, the actual composition of the compositions and the location within the gastrointestinal tract where the pharmaceutical composition is to be released, is an important consideration in terms of the present invention. Thus, where the combination of the components of the composition comprise components intended to interact with one another or with components within the aqueous medium, such as digestive enzymes or acidic components, the components and amounts thereof are selected to provide low concentrations of active agent at absorption sites and consequently low toxicologically acceptable systemic concentrations in the plasma or blood stream of treated subjects.

Components of enteric coatings which may be considered, include a selection from cellulose acetate phthalate, cellulose acetate trimellitate, celluloseacetate succinate, hydroxypropylmethylcellulose acetate succinate, methacrylic acid/ethyl acrylate, hypomellose acetate succinate, hydroxypropyl methylcellulose phthalate, and Polyvinyl acetate phthalate, or a combination thereof.

Regarding toxicology issues, note is made of the following report from Japan: "Animal toxicology studies performed in Japan on rats report as follows: "Subchronic toxicity of the mixture of $ClO_2$, $ClO_2^-$ and $ClO_3^-$ in water on rat was studied through feeding test for 90 days. Statistical analyses of variance on weight gained, food utilization efficiency, indexes of blood and serum, liver/bodyweight and kidney/bodyweight ratios, and histopathological examination on liver and kidney were carried out. The results showed that solution of $ClO_2$ and its by-products $ClO_2$— and $ClO_3$— at a concentration of 553 mg/L was not toxic."

Potentials of uses of pharmaceutical compositions of the invention are suggested by applications or administrations performed with earlier available oxidant solutions, practically invariably involving oral ingestion by means of water-diluted drinkable aqueous solutions. In one case, reference is made to a composition comprising calcium hypochlorite combined with sodium carbonate or sodium bicarbonate comprised in a gelatine capsule. A conclusion is provided to the effect that the product should be taken with large quantities of water to encourage passage thereof into the duodenum. Reported uses of earlier products include references to treatments of various types of of cancer, AIDS, pathogenic diseases, malarial parasites, hepatitis, HIV, influenza, oral care and the like. Insofar as such uses indeed appear to be justifiable, the pharmaceutical compositions of the invention should at least parallel such reported uses, but involve improved therapeutic effects by virtue of securing control over releases of active agent and absorption procedures therefor.

Consideration of above factors may include other viruses such as the mosquito-borne Dengue fever virus and others. Limited trials in Brazil, for example, suggest positive therapeutic effects on Dengue fever virally-infected patients and indeed also Zika and yellow fever infected patients.

At this point, consideration and presently confidential reference is made to an independent unpublished expert confidential analysis performed by a well-known professor of medicine at a leading university in Germany. In terms of this exhaustive analysis, the effects of oxidants on pathogenic infections harboured by subjects are explained, together with issues which may surround toxicological aspects of administration of oxidants as shortly described above. Basically, the expert analysis includes information concerned with reactions of oxidants with systemic pathogenic infections of subjects. The analysis reports inactivation conversions of pathogens and furthermore leading to active oxidants converting to inactive compounds such as water and sodium chloride. In relation to above, expert analyses performed concerned with treatment of viral infections conclude that acidic lipid cell structures comprising certain viruses (such as the Ebola virus) present points of attack which may enable destruction of the cell structure by detergents which are also employed against bacteria. Basically, the understanding involves attraction of chlorine dioxide oxidant by the acidic cell structure leading to oxidative loss of electrons and consequential bursting of the cell and killing of the virus. It appears that such activities would be selective and would not affect uninfected cellular structures. An important explanation comprised in a further expertise concerned with a clinical assessment of a tablet composition of the invention is a reference to late relapse of malaria observed during infection by *P. vivax* and *P. ovale*, indicated to exist in a latent form (hypnozoite) in human liver cells. This explanation suggests that it may be of advantage to employ a gastro-internal-tract (GIT) administration form of products of the invention, more particularly enteric-coated products, leading to first pass passage of active agents to the liver, rather than directly to the systemic system of subjects requiring treatment in at least such cases of infection.

It is generally accepted that malaria is one of the most widespread infectious diseases representing over 2 million deaths per year in Central Africa and although every medical and hygienic effort is undertaken to reduce the number, reports of WHO who report a steady increase in the number of infections as well as the development of tolerance to conventional drugs such as resochine (Chloroquine®), the antibiotic tetracycline Doxycycline® or the combination Malarone® (Atovaquon-Proguanil), all of which are not only characterised by resistance development but also of severe side effects Although the latest generation of agents employed in the treatment of malaria such as Lariam® (a chinine derivative) showed little resistance development, they are however characterized by serious side effects. And while treatment is readily available in large cities where hospital doctors as well as medical staff are able to treat acute symptoms of malaria, the inhabitants of suburban and rural areas lack such advanced care It is because in such remote areas, the general medical practitioner (GP) is only visited by patients possessed of acute symptoms of *Plasmodium falciparum* infection having reached a critical state. Especially, development of tolerance to conventional medication presents a problem in treatment of an acute infection when using the ACT (Additional or Artimisinin Combination Therapy) consisting of a dual-drug approach, one of which is always an artemisinin derivative.

Exemplary ACT products mentioned in the literature include the following commentary:

Currently artemisinin-based combination therapy (ACT) is recommended for the treatment of *P. falciparum* malaria. Fast acting artemisinin-based compounds are combined with a drug from a different class. Companion drugs include lumefantrine, mefloquine, amodiaquine, sulfadoxine/pyrimethamine, piperaquine and chlorproguanil/dapsone. Artemisinin derivatives include dihydroartemisinin, artesunate and artemether. A co-formulated drug is one in which two different drugs are combined in one tablet; this is important to ensure that both drugs are used in treatment procedures.

The benefits of ACTs are their high efficacy, fast action and the reduced likelihood of resistance developing. In order to make best use of them, particularly since no alternative is likely for a number of years, it has become critical to address issues of delivery, access and the cost of products.

Chloroquine is still the first line treatment for *P. vivax* and *P. ovale*, while primaquine can be used to treat liver stage parasites of *P. vivax*, in areas of low malaria transmission if adherence is to be ensured.

In spite of the new strategies related to ACT products employed in the treatment of malaria, there is a continuing demand for alternative therapeutic agents which do not present difficulties concerned with developments of tolerance, including side-effects. Therefore, the objective of the present invention is to ascertain the effects of, a newly formulated effervescent tablet which is easily accessible to patients in urban areas. This type of product has been determined to demonstrates a high therapeutic efficacy, is easily administered to patients, and does not exhibit the usual side effects encountered with conventional medications.

Further aspects and embodiments of the invention will be apparent to those skilled in the art given the present disclosure including the following experimental exemplification.

All documents mentioned in this specification are incorporated herein by reference in their entirety.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

Certain aspects and embodiments of the invention will now be illustrated by way of example and with reference to the figures described above.

MATERIAL AND METHODS

In terms of the present invention, it has been the overall intention to study the efficacy of a totally new medication and procedure which has thus far basically only been employed for decreasing contamination of drinking water, which has been in practical use over the past 10 years or more. The compound sodium chlorite ($NaClO_2$), when in contact with an acidic aqueous medium, converts to chlorine dioxide ($ClO_2$) which in itself acts as a highly potent oxygen radical-releaser. When chlorine dioxide attaches to the layer of a malaria trophozoite, this causes disintegration and rupturing of the outside covering of the protozoon, leading to the immediate demise of the parasite.

By the addition of sodium bicarbonate, an effervescent composition has been developed which, when exposed within an acidic aqueous medium, results in the release of carbon dioxide ($CO_2$), providing a dilution effect on the chlorine dioxide active ingredient. The chlorine dioxide is readily absorbed from saliva by the mucous membranes of the oral cavity and, after entering the blood cycle, rapidly attaches to practically any form of preexisting trophozoites. This reaction terminates within one hour after chlorine dioxide has entered the blood stream where it is converted into two inactive and neutral reaction end products, sodium chloride (NaCl) and water, in terms of the following simple chemical reaction in the presence of an exemplary carbonic acid, most conveniently acetic acid:

$$5\ NaClO_2 + C_6H_8O_7 = 4\ ClO_2 + 5\ NaCl + 2\ H_2O$$

Thus, the compressed tablet, aside from containing the prodrug sodium chlorite ($NaClO_2$) and the additive citric acid ($C_6H_8O_7$), which reacts with the chlorite to produce the $ClO_2$, have been maintained in earlier available solvent-free compressed tablets formerly employed in various treatment procedures, including the treatment of malaria, to which an artimisin extract has been added. Such addition, deemed to be a necessary component of antimalarial pharmaceutical preparations is an agent known for many years in traditional Chinese medicine as an efficient antimalarial agent but also since the the World Health Organisation (WHO) presently requires that any new pharmaceutical composition to be introduced to the market for treatment of malarial infections, should comprises a component of artimisin or its active ingredient artemisinin. All other components, other than another or other selected oxidants employed in compositions of the invention, together with the required addition artemisinin to the compositions of the present invention, however, are inert. Such other components are employed essentially only for purposes of either increasing solubilisation, for encouraging reabsorption through the mucous membranes or to improve the taste of the composition (see Table 1).

A variety of earlier successful clinical trials carried out over a number of years in several countries in Africa, such as in Nigeria, Senegal, Cameroon, Burkina Faso, and Gambia with the aid of solid solvent-free compositions for inhibiting or treating pathogenic or germicidal infections in terms of the present invention, more particularly specifically for the treatment of the malarial *Plasmodium falciparum* parasite. An example of such successful clinical trials is reported in paragraph 65 above. Of particular interest in this regard is that the composition of the invention employed in these earlier trials employed only sodium chlorite as the active oxidant, in combination with acetic acid and inert carriers and furthermore a quantity of sodium bicarbonate.

For purposes of introducing a pharmaceutical product of the present invention to the market, more extensive clinical trials directed to the treatment of malaria patients have been performed on a pilot-study basis. Such trials, recently performed in Cameroon with the aid of a pharmaceutical product of the present invention, comprises the required artimisin component (see Exemplary Table 1 below) The results of such clinical trials have been required to be made available for reference purposes to attending medical practitioners and paramedical staff engaged in the trials and also to authorities in such countries where approvals for registrations are or may be required.

Gaseous chlorine dioxide ($ClO_2$) is the preferred active molecule, to be reabsorbed through the mucous membranes and/or the intestinal lining inducing a sufficiently high serum level, more particularly and preferably following on systemic absorption through the mucous membranes. Because of the negative charge of chlorine dioxide, the chlorine dioxide is attracted by the positive charge of practically any type of parasite and, for example, by closely attaching to the outer layer of the malarial *Plasmodium falciparum*, a highly aggressive oxygen radical ($O_2^-$) is released. This oxygen radical, for the sake of stability, eliminates electrons from the outer lining of the parasite, leading to the disintegration and rupturing of this layer, which is followed by immediate demise. of the parasite

TABLE 1

Exemplary composition tablet administered to patients for treatment of parasite infection with *Plasmodium falciparum*.

| Sr. No. | Composition | Content in mg | Role in treatment |
|---|---|---|---|
| 1 | Sodium bicabonate | 44.0 | To get an effervescent formulation, at the same time being a penetration enhancer through mucous membranes of oral cavity |
| 2 | Sodium chlorite | 15.0 | The active ingredient which later converted into ClO2 |
| 3 | Arabic gum | 197.9 | An important agent to increase solubilization and absorption through the mucosal lining |
| 4 | Povidon 25 | 7.0 | A synthetic polymer vehicle for dispersing & suspending drugs and also a binder for tablets |
| 5 | Xylitab | 376.0 | A natural sweetener to increase tastiness |
| 6 | Acesulfame-Potassium | 7.0 | An artificial sweetener and also an enhancing agent for absorption |
| 7 | Prosol | 30.0 | Silicified microcrystalline cellulose, a combination of microcrystalline cellulose (MCC) and colloidal silicon dioxide (CSD) for binding properties of the tablet |
| 8 | Citric acid (540 + 110) | 65.0 | The ignition key for the formation of chlorine dioxide |
| 9 | Magnesium stearate 40% | 50.0 | An inert compound for reducing stickiness during the production process |
| 10 | *Artemisia* | 1.9 | An extract of *Artemisia annua* with oxygen radical scavenging properties, an antinflammatory and an enhancer in efficacy of antimalarial agents |

Treatment Procedure

A total dose of 75 mg of sodium chlorite comprised within 5 tablets was given 3 times per day at intervals of 8 hours. Commencing with the 5 tablets on the first day, this is followed by 2 times 3 tablets (=45 mg of sodium chlorite) at intervals of 8 hours one the following 5 days Patients are instructed to place the tablet under their tongue (sublingual) and allow the tablet to dissolve for about 10-15 minutes. The patients are not allowed to suck, chew or swallow the tablet as this may result in lowering the plasma concentration of chlorine dioxide.

Figure 2:
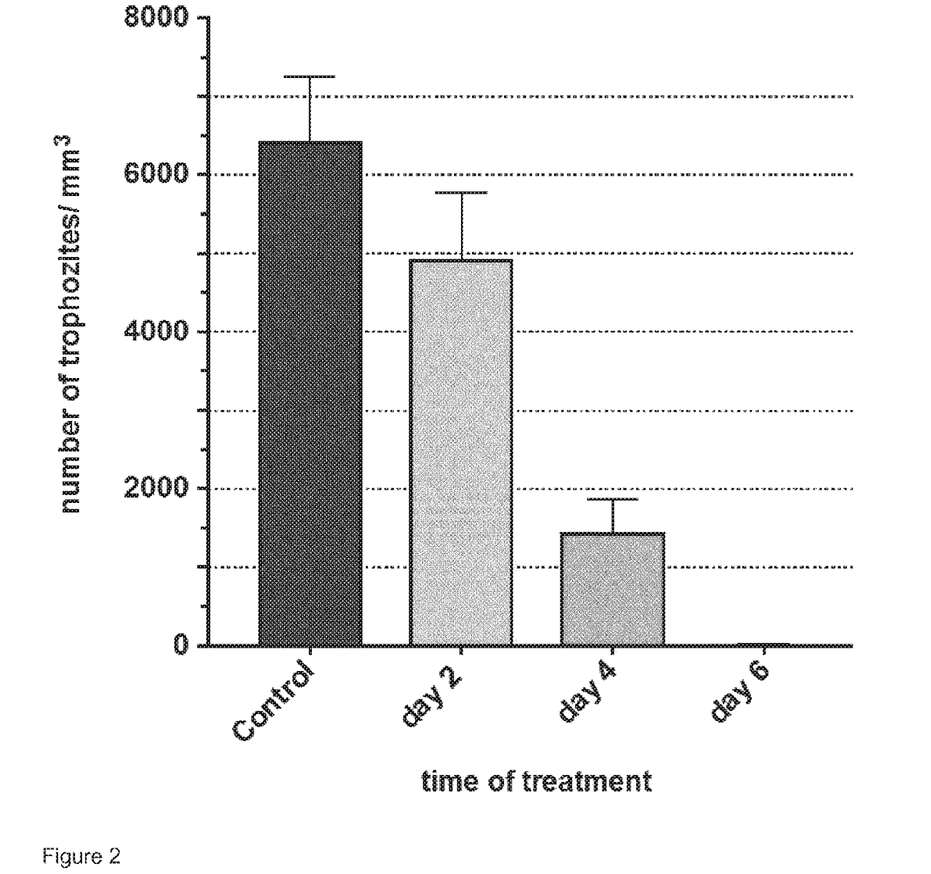
FIG. 2 shows the number of trophozites at the start of the study and at 2, 4 and 6 days after treatment. The mean count of trophozites per $mm^3$ of blood is shown.

Results of the above treatments are similarly shown in FIG. 2.

As may be observed by a comparison of FIG. 2, which relates to a second series of treatments related to a composition comparing an artimisin composition with that FIG. 1, which relates to the results obtained with earlier treatments performed with earlier first tablet forms of the invention (see paragraphs 66 and 67 above), there is essentially no difference between the results of the two series of treatments. This indication would appear to confirm that the inclusion of an artimisin component in the composition employed in the above second series of clinical trials appears, has not to led to any particular influence on the activity or the positive effects and results obtained in the first earlier series of clinical trials.

What is claimed is:

1. A pharmaceutical composition comprising:
   an essentially solid solvent-free composition, said essentially solid solvent-free composition comprising:
   one or more oxidising components selected from the group consisting of: sodium hypochlorite and potassium hypochlorite,
   wherein said one or more oxidising components are dispersible or soluble in an aqueous liquid medium,
   wherein dispersal or dissolution of said one or more oxidising components in an aqueous medium comprising at least one dispersible or soluble solid solvent-free acid component, being provided in conjunction or in combination with said one or more oxidising components comprised in the solid solvent-free composition, results in the release or generation of a molecular or ionic chlorine dioxide or a derivative thereof as an active agent within the respective aqueous liquid medium,
   wherein said essentially solid solvent-free composition comprises an absorbable therapeutically effective non-toxic amount of said one or more oxidising components absorbable by transit through the buccal cavity of a warm-blooded mammalian subject,
   wherein said one or more oxidising components are intimately admixed with at least one dispersible or soluble solid solvent-free acid component selected from the group consisting of: anhydrous citric acid,
   wherein an amount of an alkali metal carbonate or bicarbonate salt is provided in conjunction with the solid solvent-free composition, and
   wherein said pharmaceutical composition is provided as oral dosage form in a soluble sublingual dosage form, adapted to be retained in the mouth or buccal cavity by the warm-blooded mammalian subject and thereby allowing for a sublingual release of said one or more oxidising component within an acidic aqueous medium provided by simultaneous sublingual release of said at least one dispersible or soluble solid solvent-free acid component into salivary contents of the buccal cavity and thereby enabling direct systemic absorption of the active agent by absorption sites offered by the sublingual surfaces of the lining of the buccal cavity of the warm-blooded mammalian subject,
   wherein the composition comprises a proportion of sodium bicarbonate or potassium bicarbonate or a combination thereof, which is in excess of about 30% w/w of the total weight of the composition, and wherein a proportion of the one or more oxidising component in the pharmaceutical composition is selected to provide a concentration of the one or more oxidising component within the aqueous medium available in a selected body cavity of the mammalian subject that is greater than about 10 ppm and less than about 100 ppm.

2. The pharmaceutical composition according to claim 1, wherein the composition comprises an amount of the one or more oxidising component not exceeding about 5% w/w of the total weight of the composition, and wherein an amount of a dispersible or soluble alkali or alkaline earth metal chloride to provide and act as an inert composition diluent and stabiliser component of the composition and aqueous liquid medium within which the composition is dispersed or dissolved.

3. A sublingual lozenge comprising the pharmaceutical composition according to claim 1.

\* \* \* \* \*